US005797834A

United States Patent [19]
Goode

[11] Patent Number: 5,797,834
[45] Date of Patent: *Aug. 25, 1998

[54] HEARING IMPROVEMENT DEVICE

[75] Inventor: Richard Goode, Los Altos, Calif.

[73] Assignee: ReSound Corporation, Redwood City, Calif.

[*] Notice: This patent issued on a continued prosecution application filed under 37 CFR 1.53(d), and is subject to the twenty year patent term provisions of 35 U.S.C. 154(a)(2).

[21] Appl. No.: 655,773

[22] Filed: May 31, 1996

[51] Int. Cl.$^6$ .................................................. H04R 25/02
[52] U.S. Cl. .................................................. 600/25; 181/130
[58] Field of Search ............... 600/25; 607/55–57, 607/136, 137; 623/10; 381/68–69.2; 181/126, 129, 130, 132, 134–136

[56] References Cited

U.S. PATENT DOCUMENTS

| | | | |
|---|---|---|---|
| 824,993 | 7/1906 | Leonard | 181/134 |
| 1,045,917 | 12/1912 | Valiquet | 181/134 |
| 1,077,766 | 11/1913 | Von Suchorzynski . | |
| 1,446,257 | 2/1923 | Leonard . | |
| 2,738,025 | 3/1956 | Annas . | |
| 3,764,748 | 10/1973 | Branch et al. . | |
| 3,985,977 | 10/1976 | Beaty et al. . | |
| 4,014,971 | 3/1977 | Perkins . | |
| 4,281,419 | 8/1981 | Treace | 623/10 |
| 4,556,122 | 12/1985 | Goode | 181/136 |
| 4,756,312 | 7/1988 | Epley . | |
| 4,800,884 | 1/1989 | Heide et al. . | |
| 4,817,607 | 4/1989 | Tatge . | |
| 4,936,305 | 6/1990 | Ashtiani et al. . | |
| 4,957,478 | 9/1990 | Maniglia | 600/25 |
| 5,141,747 | 8/1992 | Scholz | 623/10 X |
| 5,236,455 | 8/1993 | Wilk et al. . | |
| 5,259,032 | 11/1993 | Perkins et al. | 381/68 |
| 5,381,484 | 1/1995 | Claes et al. | 381/68.6 |
| 5,425,104 | 6/1995 | Shennib | 381/68 |
| 5,578,086 | 11/1996 | Prescott | 623/10 X |

FOREIGN PATENT DOCUMENTS

| | | |
|---|---|---|
| 0291325 | 11/1988 | European Pat. Off. . |
| 2044870 | 3/1972 | Germany . |
| 3243850 | 5/1984 | Germany . |
| WO 92/03893 | 3/1992 | WIPO . |

OTHER PUBLICATIONS

William F. Decraemer, et al., "Shape and Derived Geometrical Parameters of the Adult, Human Tympanic Membrane Measured with a Phase–shift Moiré Interferometer", *Hearing Research*, vol. 51, pp. 107–122, 1991.

Richard L. Goode, et al., "Audition Via Electromagnetic Induction", *Arch Otolaryngol*, vol. 98, pp. 23–26, Jul. 1973.

J. Rutschmann, "Magnetic Audition–Auditory Stimulation by Means of Alternating Magnetic Fields Acting on a Permanent Magnet Fixed to the Eardrum", *IRE Transactions On Medical Electronics*, pp. 22–23, Mar. 1959.

*Primary Examiner*—John P. Lacyk
*Assistant Examiner*—Samuel Gilbert
*Attorney, Agent, or Firm*—Burns, Doane, Swecker & Mathis LLP

[57] ABSTRACT

A thin diaphragm for contacting an individual's tympanic membrane is sufficiently stiff and flexible to vibrate in response to audio frequencies so as to augment or over-ride the displacement of the individual's tympanic membrane in order to increase the acoustic efficiency of the tympanic membrane at all frequencies but particularly above 1000 Hz so as to improve mild hearing loss.

18 Claims, 4 Drawing Sheets

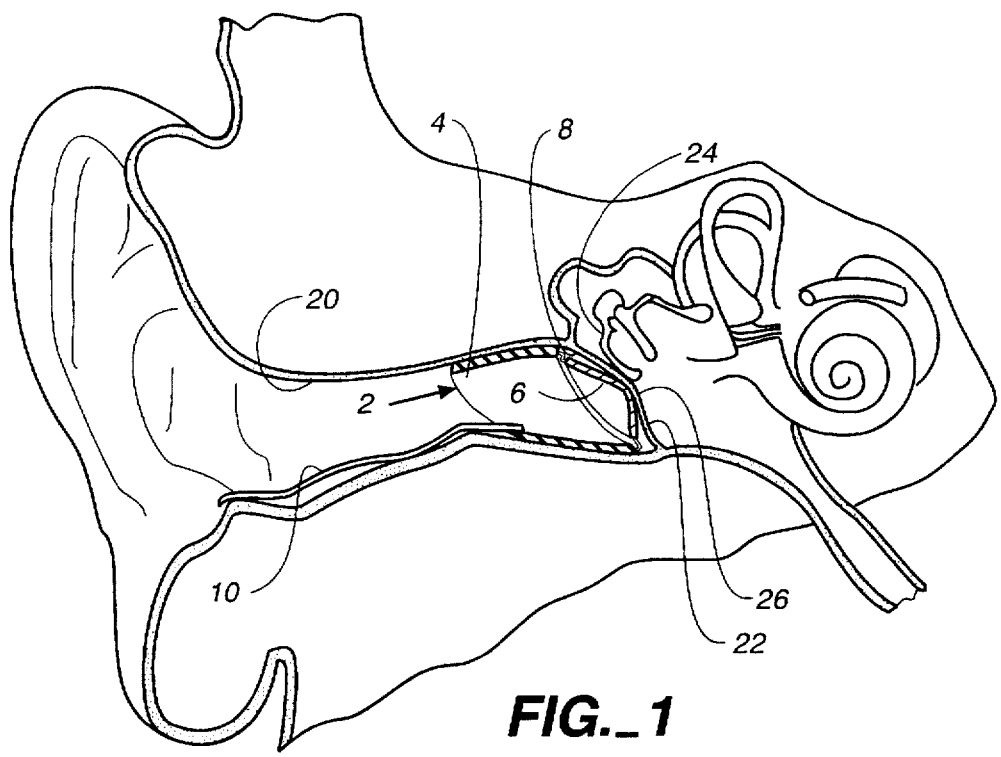
FIG._1
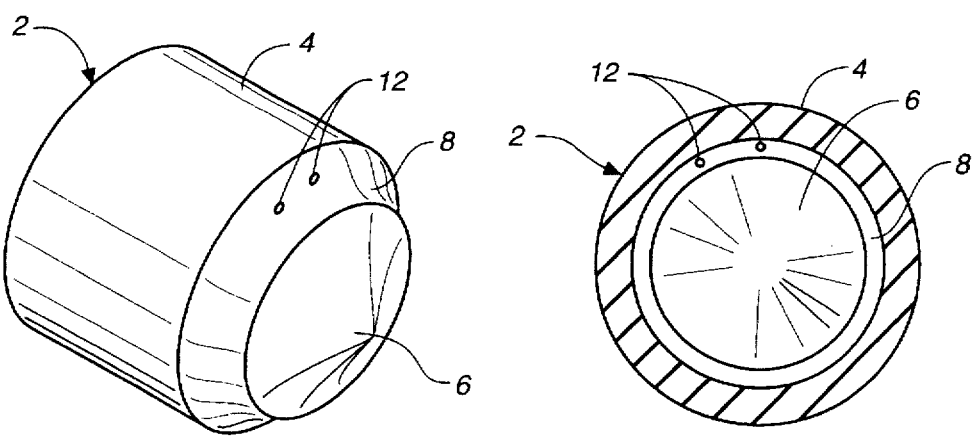
FIG._2  FIG._4

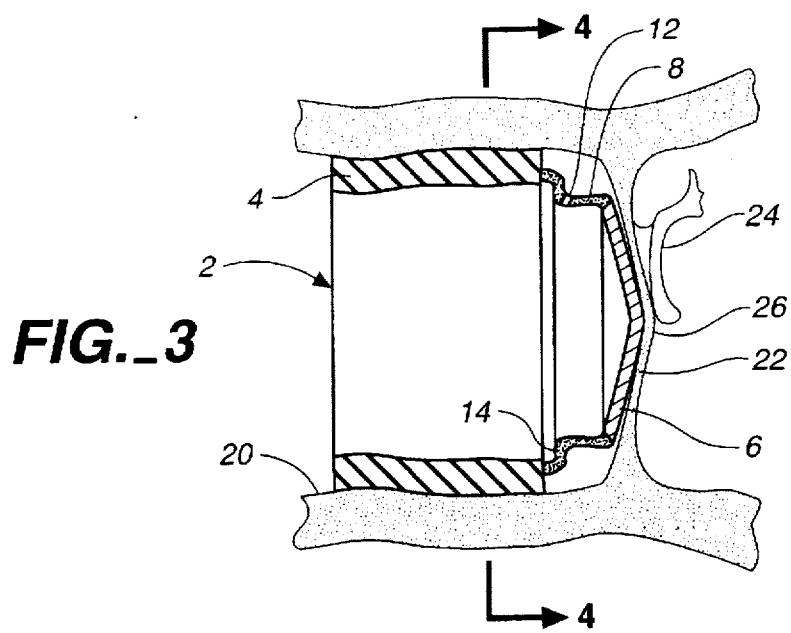
FIG._3
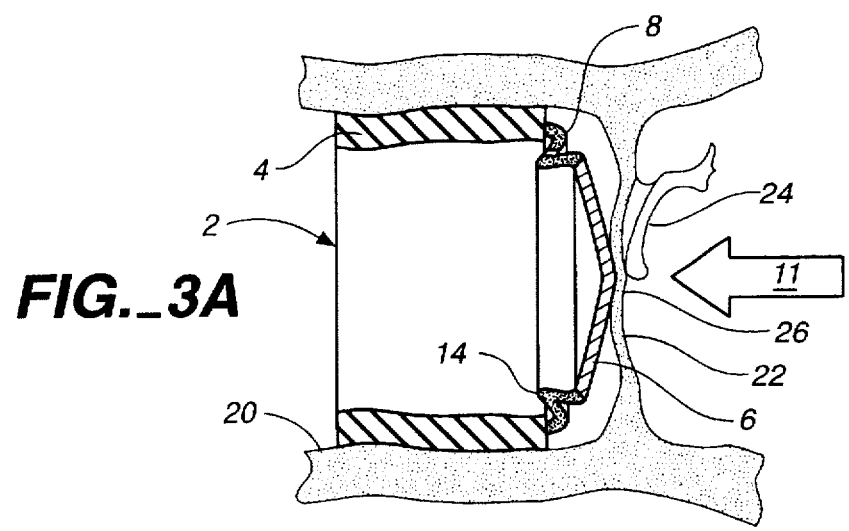
FIG._3A
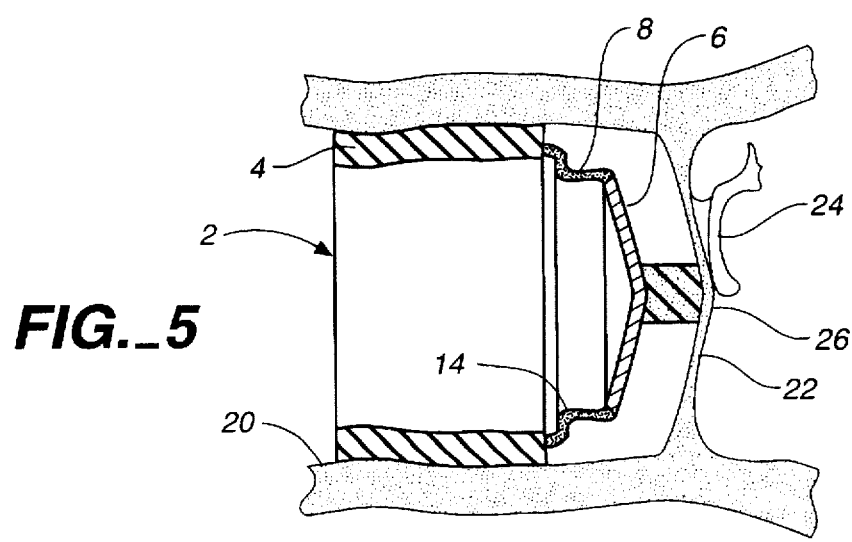
FIG._5

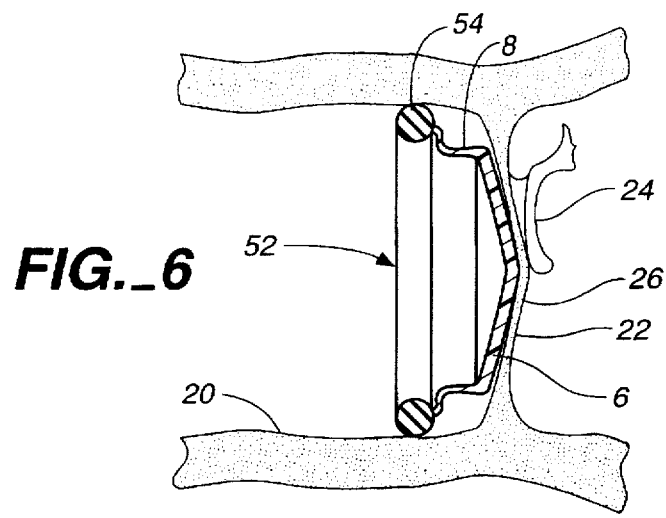
FIG._6
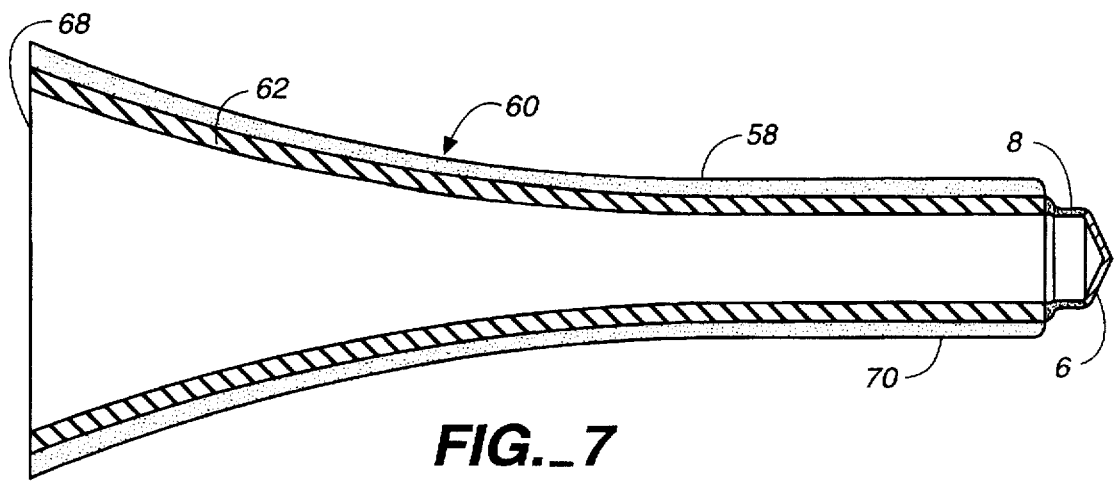
FIG._7
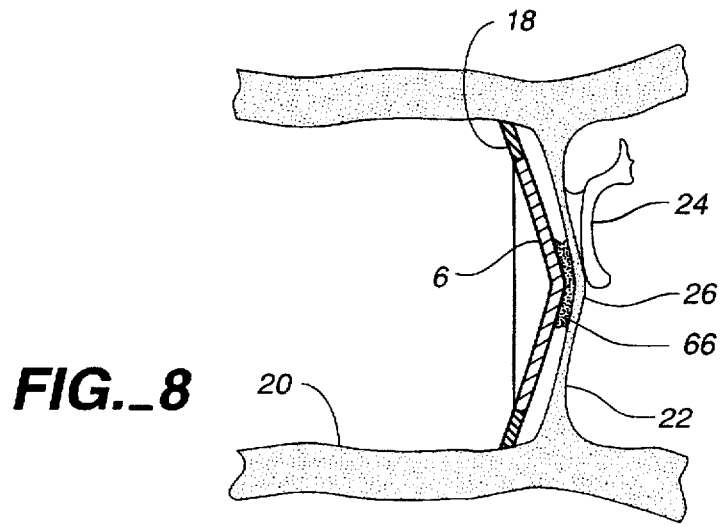
FIG._8

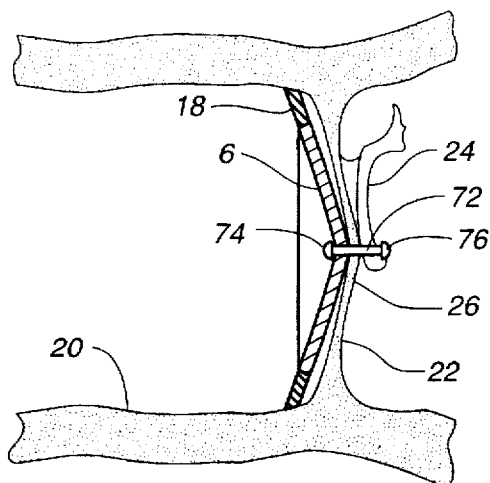
FIG._9
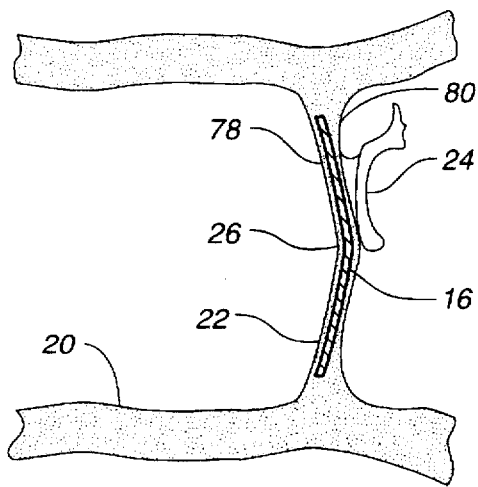
FIG._10
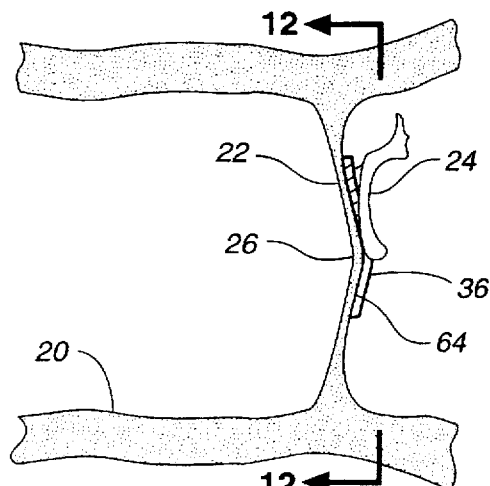
FIG._11
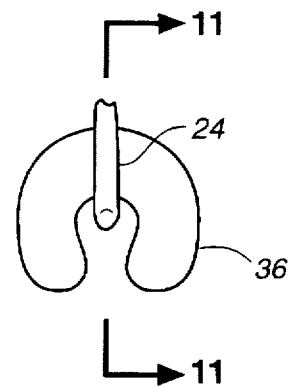
FIG._12
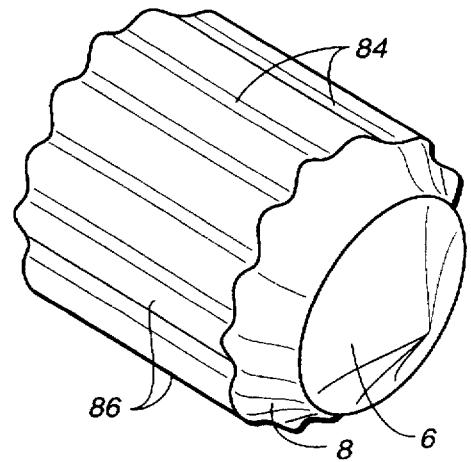
FIG._13

HEARING IMPROVEMENT DEVICE

FIELD OF THE INVENTION

The present invention relates generally to hearing improvement devices, and more particularly to a device which contacts a user's ear drum for improving the user's hearing by augmenting and/or over-riding the vibrational characteristics of the user's ear drum.

BACKGROUND OF THE INVENTION

The types of treatment given to the hearing impaired vary depending upon the type and extent of hearing loss. For example, aging and noise exposure result in hearing loss due primarily to a decrease in the nerve function in the cochlea or a reduction in the number of "hair" cells (very small, specialized cells) located within the inner ear. Hair cells are responsible for producing electrical impulses which are transmitted to the brain by the auditory nerve and perceived as sound.

Another type of hearing loss is due to abnormalities in an individual's tympanic membrane, more commonly known as the ear drum. Abnormalities of this type include perforations, scars, stretching, biological variations of the intrinsic visco-elastic properties, and tissue damage due to disease. The most common and often the most impairing of these abnormalities is a perforation of the tympanic membrane. Tympanic membrane perforations are usually corrected by surgery. However, other less impairing abnormalities, such as an intact but scarred or flaccid tympanic membrane, are rarely surgically corrected because the results are not regularly predictable and may not be worth the expense and risks associated with surgery.

It is well known that the acoustic function of the tympanic membrane is to transform sound pressure at its outer surface into vibration of the malleus, the outermost, ear bone that is incorporated in part within the tympanic membrane. This vibration is transferred to the other two connected earbones, the incus and stapes, to produce movement of the cochlear fluid that stimulates the hair cells and produces the sensation of sound. The efficiency of the tympanic membrane can be determined by measuring malleus displacement or velocity in response to a constant sound pressure level (SPL) at its outer surface at the important hearing frequencies. The higher the malleus displacement or velocity for a given SPL, the higher the efficiency, all else being equal. Malleus vibration is conventionally measured at the umbo, located near the center of the tympanic membrane, so the greater the umbo displacement or velocity in response to a given sound pressure at the surface of the tympanic membrane, the greater the tympanic membrane efficiency, everything else being equal. It is also known that above 1000 Hz, the efficiency of the human tympanic membrane decreases at a rate of 6 to 8 dB/octave. This is in contrast to other species, such as the guinea pig, where the tympanic membrane efficiency remains high up to 10.000 Hz.

In addition, it has been shown that there is a 20 to 25 dB variation in normal tympanic membrane efficiency at key hearing frequencies (250, 500, 1000, 1500, 2000, 3000, 4000, 6000 Hz). Some tympanic membranes are much more efficient than others, in transferring energy to the malleus, probably due to differences in the visco-elastic properties of the tympanic membrane. Human tympanic membranes which are intact but have been damaged by previous infection, trauma, etc. are regularly worse in acoustic efficiency. Diaphragms, such as used in microphones, can be designed to be extremely efficient in converting sound pressure at their outer surface into vibration at their center, including higher frequencies above 1000 Hz. These diaphragms are made of a variety of materials including mylar, aluminum, stainless steel, polyethylene, polypropylene, titanium, beryllium, etc. Surgical substitution of these extremely efficient acoustical diaphragms for the human tympanic membrane is not practical at this time for a variety of reasons.

For individuals with moderate to profound hearing impairment, the usual treatment is an electronic hearing aid. Although capable of substantially improving hearing, hearing aids are very expensive and have other inherent drawbacks, such as feedback, the need to replace batteries, and small, difficult to manipulate controls and switches. For those with moderate to profound hearing impairment of this kind, these drawbacks may be immaterial; however, for those with only mild to moderate hearing loss, the drawbacks of a hearing aid may not outweigh its advantages.

SUMMARY OF THE INVENTION

Placing a highly efficient diaphragm adjacent to the outer surface of the tympanic membrane in accordance with the present invention allows improvement or augmentation of normal tympanic membrane acoustic function, particularly at higher frequencies from about 1000 to 6000 Hz where the human tympanic membrane is most inefficient. In addition, this is the frequency range most commonly affected in cases of mild hearing loss. By placing an acoustically efficient diaphragm in contact with the tympanic membrane, human tympanic membrane performance is improved, improving hearing and correcting mild hearing loss whether due to impaired tympanic membrane function alone or sensorineural hearing loss due to hair cell or nerve dysfunction.

In accordance with the present invention, a thin diaphragm for contacting an individual's tympanic membrane is sufficiently stiff and flexible (i.e., efficient, such that it is more flexible in the center and stiffer at the outer edges) to vibrate in response to key hearing frequencies so as to augment or over-ride the displacement of the tympanic membrane so as to improve hearing.

In one embodiment, there is provided a device comprising an acoustically efficient diaphragm that contacts the individual's tympanic membrane, the diaphragm being sufficiently stiff to provide optimal performance in the about 200 to 6000 Hz frequency range and improve function of the tympanic membrane at these frequencies.

BRIEF DESCRIPTION OF THE DRAWING

FIG. 1 is a diagrammatic cross-sectional view showing the approximate placement of one embodiment of the hearing device of the present invention within the ear canal.

FIG. 2 is a diagrammatic isometric view of one embodiment of the hearing device.

FIG. 3 is an enlarged, diagrammatic cross-sectional view of the embodiment of FIG. 1 in a first position.

FIG. 3A is an enlarged, diagrammatic cross-sectional view of the embodiment of FIG. 1 in a second position.

FIG. 4 is a diagrammatic bottom view of the hearing device of FIG. 3.

FIG. 5 is a diagrammatic cross-sectional view of another embodiment of the present invention located within the ear canal.

FIG. 6 is a diagrammatic cross-sectional view of another embodiment of the present invention located within the ear canal.

FIG. 7 is a diagrammatic cross-sectional view of another embodiment of the present invention.

FIG. 8 is a diagrammatic cross-sectional view of another embodiment of the present invention contacting the tympanic membrane.

FIG. 9 is a diagrammatic cross-sectional view of another embodiment of the present invention attached to the malleus.

FIG. 10 is a diagrammatic cross-sectional view of another embodiment of the present invention.

FIG. 11 is a diagrammatic cross-sectional view of another embodiment of the present invention.

FIG. 12 is a diagrammatic rear view of the hearing device of FIG. 11.

FIG. 13 is a diagrammatic isometric view of another embodiment of the hearing device.

DETAILED DESCRIPTION OF THE PREFERRED EMBODIMENT

The present invention provides an inexpensive, easy to use and maintain apparatus that improves mild to moderate hearing loss by augmenting and/or over-riding the vibrational characteristics (i.e., displacements) of the tympanic membrane. Mild to moderate hearing loss is defined as hearing thresholds from 25 to 60 db hearing level (HL) in the 250 to 6000 Hz frequency range. The present invention improves an inefficient ear whether the inefficiency is due to a flaccid or scarred tympanic membrane or an inefficient normal tympanic membrane. Typically, the tympanic membrane 22 and the walls of the ear canal 20 are obliquely positioned with respect to each other as shown in FIG. 1. However, for ease of illustration, the ear canal and tympanic membrane are shown substantially perpendicular to one another in FIGS. 2, 3, 3A, 5, 6, and 8–12. Referring initially to FIGS. 1 and 2, one embodiment of hearing device 2 of the present invention is positioned within ear canal 20. In one embodiment, hearing device 2 is a convex diaphragm 6 attached to end of holder 4 with a compliant skirt or membrane 8. Attached to the outermost end of holder 4 is a tether 10 for removal of device 2. Tether 10 may comprise a string or be of material that is stiffer, and is long enough so that a user can use his fingers to pull it out of his ear and short enough to be inconspicuous.

In one embodiment, holder 4 has an approximately cylindrical shape, is hollow, and is designed to fit comfortably and snugly within ear canal 20. Holder 4 may be custom-designed to fit an individual ear canal, or be generically designed to fit a large variety of shapes and sizes. For custom fitting, holders are preferably made of vinyl, silicone rubber, acrylic or a biocompatible material having similar properties. On the other hand, generic tubes are preferably made of a deformable yet durable material such as a visco-elastic polymer which conforms to the contours of individual ear canals upon insertion. In another embodiment (FIG. 13), the holder contacts the ear canal at only a few locations to minimize wax and skin collection under the holder. The depressions 84 between the plurality of contact points 86 do not contact the surface of the ear canal. Generally, there can be any number of contact points and depressions ranging from only two contact points to an infinite number (i.e., the holder of FIG. 2). Holder 4 can be designed to extend into the outer aspect of the ear canal so that it can be grasped by the patient for insertion or removal in lieu of tether 10.

The purpose of diaphragm 6 is to improve the performance characteristics, specifically resonant frequency and displacement, of an individual's tympanic membrane. Diaphragm 6 rests against the user's tympanic membrane to achieve up to a peak-to-peak umbo displacement of 0.1 micron at sound frequencies in the range of about 1500 to about 4000 Hz, more preferably about 1000 to about 6000 Hz, and most preferably about 200 to about 6000 Hz, in response to a 80 dB SPL input at the ear drum. The dimensions (e.g., diameter, thickness, curvature), properties (e.g., rigidity, resonant frequency, displacement), and positioning of diaphragm 6 are dependent upon the physiological dimensions and the performance characteristics of the individual user's ear canal and tympanic membrane, as one of ordinary skill in the art will recognize based on, for example, the principles discussed in Schaum's Outline Series, "The Theory and Problems of Acoustics", William W. Seto, (McGraw-Hill Book Co. 1971).

In order to achieve the desired resonant frequency and peak-to-peak displacement, diaphragm 6 is comprised of a thin but stiff low mass material with appropriate tension. In acoustics research, this type of object is often times referred to generally as, a "thin shell". These devices are generally thinner in the middle so that they perform similar to a kettle drum with a generally stiff or fixed outer edge and a vibrating middle. Suitable materials for the diaphragm include, but are not limited to, titanium, stainless steel, polyurethane, polypropylene, mylar, composite material containing carbon fibers, titanium mesh, collagen, biocompatible plastic, etc. These materials are preferred because they can provide an extremely thin diaphragm, preferably in the range of about 0.01 to about 1.0 mm, while providing sufficient stiffness that the diaphragm resonates in response to normal auditory influences such as speech and displaces the user's tympanic membrane in an augmented manner. Typically, the diaphragm is sufficiently thin, light and/or stiff to have a resonant frequency greater than about 200 Hz to improve frequency performance from about 200 to about 6000 Hz, more preferably greater than about 1000 Hz to improve higher frequency performance from about 1000 Hz to about 6000 Hz because this is frequently the range of frequencies that need to be boosted for an individual with mild hearing loss.

If the user's tympanic membrane is relatively normal in function and the user has hearing loss due to a decrease in the nerve function in the cochlea or a reduction in the number of "hair cells", then the diaphragm vibrates so as to augment the displacement of the tympanic membrane particularly at higher frequencies above about 1000 Hz (similar to the way an electronic hearing aid amplifies sound to provide additional stimulus to the ear). If the user's tympanic membrane is scarred or flaccid, the diaphragm functions in the same way but provides improved performance compared to the normal tympanic membrane situation. There are methods to determine clinically which tympanic membranes are efficient and which are not including impedance testing and laser doppler vibrometry. In certain situations, the diaphragm may be used in combination with an electronic hearing aid, as well.

In one embodiment, diaphragm 6 has a slightly convex shape and a diameter preferably within the range of about 3 to about 10 mm. However, the shape of diaphragm 6 may be any of a number of different shapes and sizes including but not limited to a cone-shape, sometimes referred to as a "thin shell", dome-shaped, hemi-spherical, etc. that vibrate and displace the tympanic membrane in the desired manner.

The optimum position for the hearing device is such that diaphragm 6 touches the center or umbo portion 26 of a user's tympanic membrane 22. This is approximately where the malleus 24, the outermost of the three middle ear bones or ossicles, is located within the tympanic membrane 22. Due to its slightly convex shape, about the center ¼ to ⅔ of the total surface area of diaphragm 6 comes into contact with tympanic membrane 22. It has been discovered that in a preferred embodiment, the contact area of the diaphragm with the tympanic membrane should be between about 50 to about 90 percent of the diameter of the tympanic membrane.

Diaphragm 6 serves to coordinate the movement of the area of the tympanic membrane in contact with it, improving the efficiency of the tympanic membrane. Additionally, diaphragm 6 "stiffens" the tympanic membrane, raising its resonant frequency and improving its acoustic characteristics, particularly in the higher frequency range of human speech, i.e., about 1000 to about 6000 Hz. The diaphragm can also be designed to improve function at lower frequencies as well depending on the type of hearing loss such as between about 200 Hz and about 6000 Hz. With the diaphragm of the present invention in contact with the tympanic membrane, the umbo typically has a peak-to-peak displacement of about 0.1 micron or more for sound frequencies in the range of about 1000 to about 4000 Hz and a peak-to-peak displacement of about 0.05 micron or more for frequencies above about 4000 Hz in response to an 80 dB SPL input at the outer surface of the diaphragm. In comparison, the peak-to-peak displacements for the same input for an individual having an average tympanic membrane performance is 0.03 micron at 1000 Hz, and below, decreasing to 0.015 at 2000 Hz, and 0.007 at 4000 Hz. Thus, a 10 to 20 dB amplification occurs with the use of the diaphragm.

Referring to FIGS. 3 and 3A, in one embodiment, attached to and fully encircling the perimeter of diaphragm 6 and the perimeter of the inner end of holder 4 is a skirt or membrane 8 made of a compliant material. Compliant membrane 8 serves dual purposes of supporting diaphragm 6 so that it maintains contact with tympanic membrane 22, and of preventing sound from going around the outer edge of diaphragm 6 in order to minimize any cancellation by sound that reflects off the tympanic membrane and against the back surface of the diaphragm thus affecting the function of diaphragm 6.

FIG. 3 illustrates membrane 8 in a relaxed state having a bend 14. Membrane 8 allows for relatively larger displacements of diaphragm 6, such as those that occur during a cough or sneeze. Specifically, bend 14 collapses in response to a force 11 (FIG. 3A) such as occurs during a cough or sneeze to allow the malleus 24, tympanic membrane 22 and diaphragm 6 to move without dislodging holder 4.

In order to prevent the build up of air pressure within the ear, especially when going from high to low or low to high atmospheric pressure (e.g., on an airplane), there is provided one or more vent holes 12. One vent hole 12 is sufficient for adjusting pressure, however, more are preferable in case one becomes obstructed by wax buildup. FIG. 4 shows a bottom view of diaphragm 6 and its accompanying membrane 8 having bend 14 and vent holes 12. In a similar fashion, the diaphragm can have openings or perforations therethrough.

Referring now to FIG. 5, in another embodiment, holder 4, membrane 8, and diaphragm 6 are identical to the embodiment described above, however, in addition, a slightly compressible bumper 50 is mounted to the center of diaphragm 6, contacting the umbo area 26 of tympanic membrane 22. Bumper 50 generally has a hollow or solid cylindrical shape, having a diameter approximately ⅒ to ⅔ that of diaphragm 6. Bumper 50 can be comprised of many different compliant but relatively stiff materials (e.g., silicon rubber, plastic or a composite thereof). The purpose of bumper 50 is to ensure that contact is maintained with tympanic membrane 22 despite relatively small tympanic membrane displacements due to swallowing, coughing, etc.

Referring now to FIG. 6, there is shown another embodiment of the hearing improvement device of the present invention. Hearing device 52 comprises holder 54, and diaphragm 6 interconnected by means of a compliant skirt 8. Holder 54, compliant skirt 8 and diaphragm 6 have the same properties, and variations thereof, as holder 4, compliant membrane 8 and diaphragm 6, respectively, of hearing device 2 of FIG. 1. However, here, holder 54 has an o-ring configuration rather than a cylindrical configuration. This embodiment has the advantage of having less surface area which reduces the amount of ear wax that can buildup on the holder. The holder 54 may not be in continuous contact with the ear canal but be raised in several areas to minimize wax and skin build up, as described with respect to FIG. 13.

In another embodiment of the present invention, illustrated in FIG. 7, hearing improvement device 60 improves upon that part of the hearing deficiency due to an acoustic inefficiency of the ear canal resonance. Hearing device 60 is comprised of an exponential horn 62 coupled to a diaphragm 6 by means of a compliant skirt 8. Here, again, diaphragm 6 and compliant skirt 8 have the same characteristics and dimensions, with variations thereof, as those corresponding elements of the other embodiments previously discussed. Exponential horn 62 has a length slightly more than that of the ear canal (not shown), typically about 4.0 to about 5.0 cm. This length facilitates insertion and removal of the hearing device by the user without the assistance of a physician. Ends 68 (the "mouth") and 70 (the "throat") of horn 62 have diameters measuring approximately 2 to 2.5 cm and about 3 to 10 mm, respectively. The exponential taper of horn 62 is generally known by one of ordinary skill in the art. The exponential taper of horn 62 produces up to a 20 dB gain as sound in the frequency range of about 1000 to about 6000 Hz passes therethrough to diaphragm 6. Horn 62 can be parabolic, conical, exponential, or any combination of these. Horn 62 is typically made of material that is hard and smooth on the inside so as not to absorb or dampen sound as it passes through the horn. The horn can be covered with a soft cover 58 so as to fit conformably and comfortably in the ear canal. Suitable materials, for example, include a silicon rubber shell with an internal lining of methylmethacrylate or other hard plastics having similar properties. An opening near the throat of the horn may be included to allow lower frequency sound to reach the outer tympanic membrane. The diameter of the opening, usually about 2 to 5 mm, has an acoustic impedance that prevents higher frequency sound above about 1000, or above about 2000 Hz, from passing through the hole out of the horn. This allows lower frequency sounds, below the cutoff frequency of the horn, to be heard.

Two other embodiments of the present invention (FIGS. 8 and 9) do not include a holder. In FIG. 8, diaphragm 6 is in contact with the tympanic membrane 22. Diaphragm 6 is attached to the outer surface of the tympanic membrane 22 with adhesive 66. FIG. 9 illustrates a similar embodiment having a diaphragm 6 in contact with tympanic membrane 22. Diaphragm 6 is held in place with an elongated clip or pin 72 which has been surgically inserted, by techniques commonly known among ear surgeons, through tympanic membrane 22 at umbo portion 26 and affixed to malleus 24. Pin 72 is fastened to the center of diaphragm 6 at a first end 74 and fastened to malleus 24 at the other end 76 of pin 98.

Pin 98 is comprised of a metal wire or screw, such as titanium, or any other suitable means for fastening the diaphragm to the malleus.

These embodiments typically provide a mean 12 dB increase in the efficiency for an average tympanic membrane 22 for sound in the range of about 1000 to about 6000 Hz, more preferably in the range of about 200 Hz to about 6000 Hz. Larger increases are achieved for tympanic membranes with less than average function. These embodiments can also have a skirt 18 that prevents sound from reflecting off the tympanic membrane and against the back surface of the diaphragm as discussed previously with respect to the cancellation effect. As will be appreciated by one of ordinary skill in the art, the material used and the vibrational characteristics of the diaphragm 6 will have to be adjusted depending on the method used for keeping the diaphragm in contact with the tympanic membrane because each of the different methods have different dampening effects on the characteristics of the diaphragm.

Referring now to FIGS. 10–12, there is shown two other embodiments of the present invention. FIG. 10 shows a diaphragm 16 that has been surgically implanted, using commonly known otosurgical techniques, within the tympanic membrane 22 between the outer epithelium 78 and the inner mucus membrane 80. Diaphragm 16 is comprised of materials (e.g., titanium mesh, collagen or biocompatible plastic) which perform with the desired characteristics as discussed previously for augmenting and/or over-riding the vibrational characteristics of the tympanic membrane. Diaphragm 16 typically has a diameter in the range of about 3 to about 8 mm and a thickness of about 10 to about 100 microns, depending on the dimensions of the individual user's tympanic membrane.

FIGS. 11 and 12 illustrate a variation of the embodiment disclosed in FIG. 10. Here, diaphragm 36 has been surgically inserted, using commonly known otosurgical techniques, adjacent to the inner surface 64 of tympanic membrane 22, between tympanic membrane 22 and malleus handle 24. As shown in FIG. 12, diaphragm 36 has a horseshoe shape and is held in place against tympanic membrane 22 with the malleus 24. Diaphragm 36 is positioned such that the opening of the horseshoe is on the bottom. Diaphragm 36 typically has an overall width within the range of about 3 to about 8 millimeters and a thickness in the range of about 10 to about 100 microns depending on the dimensions of the individual user's tympanic membrane and malleus.

EXAMPLE

A 10 mm diameter, 0.1 mm thick, circular Mylar diaphragm fixed at its circumference in the ear canal was placed in contact with the majority of a tympanic membrane. The diaphragm produced a greater than 20 dB increase in stapes displacement from 200 to 8000 Hz compared with the baseline condition prior to application of the diaphragm. The sound input was a flat 90 dB SPL. The measurement was made in a human temporal bone model using a laser doppler vibrometer to measure stapes displacement. Stapes displacement is proportional to umbo displacement in the human ear and was used in these measurements instead of umbo displacement. Details of the measurement method are described in the reference Goode et al., "New Knowledge About the Function of the Human Middle Ear: Development of an Improved Analog Model", *Amer. Journal of Otology*, 15: 145–154, 1994.

The foregoing disclosure and description of the invention are illustrative and explanatory of the invention. Various changes in the size, shape, materials and components, as well as in the details of the illustrated construction and method may be made without departing from the spirit of the invention, all of which are contemplated as falling within the scope of the appended claims.

What is claimed is:

1. A device for improving an individual's hearing, comprising:

a diaphragm having an outer edge portion and a center portion wherein said center portion is more flexible than said outer edge portion, adapted for contacting the individual's tympanic membrane, the diaphragm being sufficiently efficient to vibrate in response to sound stimuli so as to displace the tympanic membrane.

2. The device of claim 1 wherein the diaphragm has a resonant frequency above about 200 Hz.

3. The device of claim 2 wherein the diaphragm has a thickness in a range of about 0.01 to about 1.0 mm and a diameter in a range of about 3 to about 10.0 millimeters.

4. The device of claim 3 wherein the diaphragm is a material selected from the group consisting of titanium, stainless steel, polyurethane, polypropylene, mylar, and a composite material containing carbon fibers.

5. The device of claim 2 wherein the diaphragm has a thickness in a range of about 10 to about 100 microns and a diameter in a range of about 3 to about 8 millimeters.

6. The device of claim 5 wherein the diaphragm is a material selected from the group consisting of titanium mesh, collagen or biocompatible plastic.

7. The device of claim 1 wherein the diaphragm has a resonant frequency selected from a range of about 200 to about 6000 Hz.

8. The device of claim 1 further comprising:

a holder connected to the diaphragm for maintaining the diaphragm against the tympanic membrane.

9. The device of claim 8 wherein the holder is attached to an outer edge of the diaphragm by a compliant member.

10. The device of claim 9 wherein the holder is a horn.

11. The device of claim 8 wherein the holder is an adhesive.

12. The device of claim 8 wherein the holder is a pin for attaching the diaphragm to a malleus of the individual.

13. The device of claim 8 wherein the holder is a clamp for attaching the diaphragm to a malleus of the individual.

14. The device of claim 1 wherein the diaphragm is adapted to contact an outer surface of the tympanic membrane.

15. The device of claim 1 wherein the diaphragm is adapted to contact an inner surface of the tympanic membrane.

16. The device of claim 1 wherein the diaphragm is adapted to be implanted in the tympanic membrane.

17. A device for improving an individual's hearing, comprising:

a diaphragm adapted for contacting the individual's tympanic membrane, the diaphragm being sufficiently efficient to vibrate in response to sound stimuli so as to displace the tympanic membrane; and a holder attached to an outer edge of the diaphragm by a compliant member adapted for maintaining the diaphragm against the tympanic membrane, wherein the compliant member has at least one hole therethrough to minimize any differential between the air pressure on each side of the compliant member when the device is contacting the tympanic membrane.

18. A device for improving an individual's hearing, comprising:

a diaphragm adapted for contacting the individual's tympanic membrane, the diaphragm being sufficiently efficient to vibrate in response to sound stimuli so as to displace the tympanic membrane; and a bumper attached to an outer surface of the diaphragm adapted for maintaining the diaphragm against the tympanic membrane.

* * * * *